(12) United States Patent
Weinberger

(10) Patent No.: US 6,527,692 B1
(45) Date of Patent: Mar. 4, 2003

(54) RADIATION CATHETERS OPTIMIZED FOR STEPPED DELIVERY TECHNIQUE

(75) Inventor: Judah Z. Weinberger, Teaneck, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/444,321

(22) Filed: Nov. 19, 1999

(51) Int. Cl.[7] .......................... A61N 5/00; A61M 29/00
(52) U.S. Cl. ................................ 600/3; 606/194
(58) Field of Search .................... 600/3, 5; 606/194, 606/15; 604/53

(56) References Cited

U.S. PATENT DOCUMENTS

| | | | | |
|---|---|---|---|---|
| 5,616,114 A | * | 4/1997 | Thornton et al. | 600/3 |
| 5,782,740 A | | 7/1998 | Schneiderman | |
| 5,797,948 A | * | 8/1998 | Dunham | 606/194 |
| 5,833,650 A | | 11/1998 | Imran | |
| 5,910,101 A | | 6/1999 | Andrews et al. | |
| 5,954,693 A | | 9/1999 | Barry | |
| 5,976,106 A | | 11/1999 | Verin et al. | |
| 6,059,713 A | * | 5/2000 | Urick et al. | 600/3 |
| 6,135,981 A | | 10/2000 | Dyke | |
| 6,251,059 B1 | * | 6/2001 | Apple et al. | 600/3 |

* cited by examiner

Primary Examiner—Eric F. Winakur
Assistant Examiner—Nikita R Veniaminov
(74) Attorney, Agent, or Firm—John P. White; Cooper & Dunham LLP

(57) ABSTRACT

A radiation catheter for intraluminal treatment of a patient has a plurality of separably inflatable and deflatable balloon segments located along the length of the catheter, and a radiation source within a lumen of the catheter. As the radiation source is moved, one or more balloon segments closest to the source is inflated with the remainder deflated thereby allowing blood to perfuse in areas where inflation of the segments is not needed to effect centering of the source in the luminal structure.

19 Claims, 3 Drawing Sheets

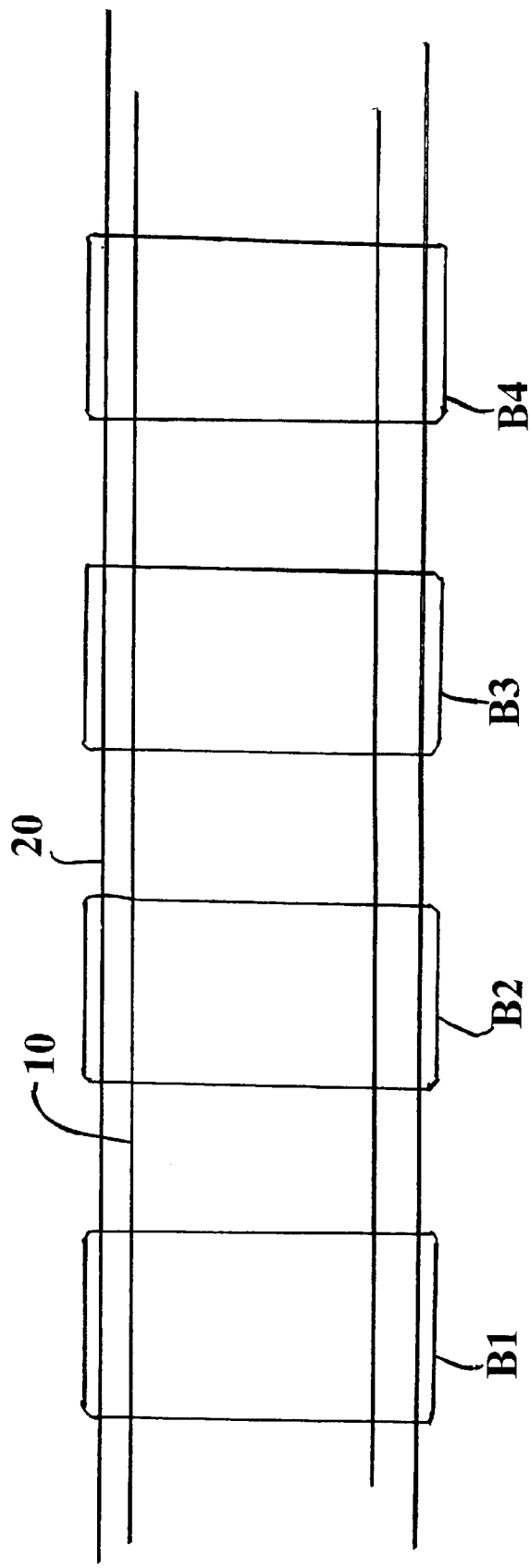

RADIATION CATHETERS OPTIMIZED FOR STEPPED DELIVERY TECHNIQUE

BACKGROUND OF THE INVENTION

The present invention relates to radiation delivery catheters having inflation balloons, and more particularly to radiation delivery catheters having a plurality of inflation balloons or other means independently inflatable for providing stepped radiation delivery and treatment.

Radiation catheters have been used for delivering radioactive material to a luminal structure, such as a vein or artery of a patient, for radiation treatment of the inner wall. When treating a longitudinal section of a vein or artery, for example, the radiation source is may be shorter than the length of the section to be treated. Consequently, the radiation source is stepped through portions of the full treatment region. In such treatment, it is highly desirable to center the radiation source axially within the lumen so that the radiation dosage is generally uniform throughout the full circumference of the luminal structure. Otherwise some portions of the structure will receive an excessive dose of radiation and/or an insufficient dose of radiation.

Various centering arrangements have been proposed. However, the centering arrangements typically block off or unduly restrict blood flow in the region that is being treated, or block off or restrict blood flow for longer time than is necessary to obtain uniform radiation dosage delivery. This is undesirable because the blood should be permitted to perfuse in as large a region as possible to minimize tissue ischemia.

The present invention is directed to an apparatus and method for providing stepped delivery of radiation in a radiation catheter to optimize radiation delivery while permitting good blood perfusion.

SUMMARY OF THE INVENTION

An object of the present invention is to allow multiple vascular radiation dwell sites of a patient's luminal structure, such as a vein or artery, without also requiring occlusion of a large segment of the vein or artery with a centering mechanism. The centering mechanism, which may be a plurality of balloons or balloon segments, each having nominal longitudinal dimension compared to the total dwell length of the dwell sites, are separably inflatable and deflatable.

According to one form of the invention, provided is a radiation catheter for treating a luminal structure of a patient, comprising a catheter having at least one lumen at least two balloon segments located at different longitudinal extents of the catheter, the segments being separably inflatable and deflatable. A radiation source may be provided movable within the lumen of the catheter, whereby the balloon segment nearest the source is inflatable to center the radiation source radially in the luminal structure, and deflatable when not needed to center the radiation source.

Other objects and advantages will become apparent from the following detailed description of the preferred embodiment, claims and drawings.

BRIEF DESCRIPTION OF THE DRAWINGS

FIG. 3 is a side view of another radiation delivery catheter where the balloons are mounted on a sleeve which receives the catheter therein.

DETAILED DESCRIPTION OF THE PREFERRED EMBODIMENT

A preferred embodiment will be described, to enable one skilled in the art how to make and use the invention. However, the scope of the invention is not limited to the preferred embodiment.

A preferred embodiment of the present invention will be described in the context of its use in a vein or artery, but is not so limited, as it can be used in any luminal structure.

According to one form of the invention, provided is a radiation catheter for treating a luminal structure of a patient, comprising a catheter having at least one lumen at least two balloon segments located at different longitudinal extents of the catheter, the segments being separably inflatable and deflatable. A radiation source may be provided movable within the lumen of the catheter, whereby the balloon segment nearest the source is inflatable to center the radiation source radially in the luminal structure, and deflatable when not needed to center the radiation source.

The balloon segments may comprise a plurality of donut, cylindrical or lobulated shaped balloons, or may comprise segments of a balloon spirally wound around the catheter. The radiation source may be a wire with radiation pellets mounted on the wire or affixed to the wire by some alternative means. The balloon segments may be two or greater, and two adjacent balloon segments may be inflated at the same or plurality of times. The balloon segments may be mounted directly to the catheter, or may be mounted onto a tube which slidably receives the catheter. Perfusion holes may be provided to permit fluid to flow inside the catheter around an inflated balloon segment.

Figure 1:
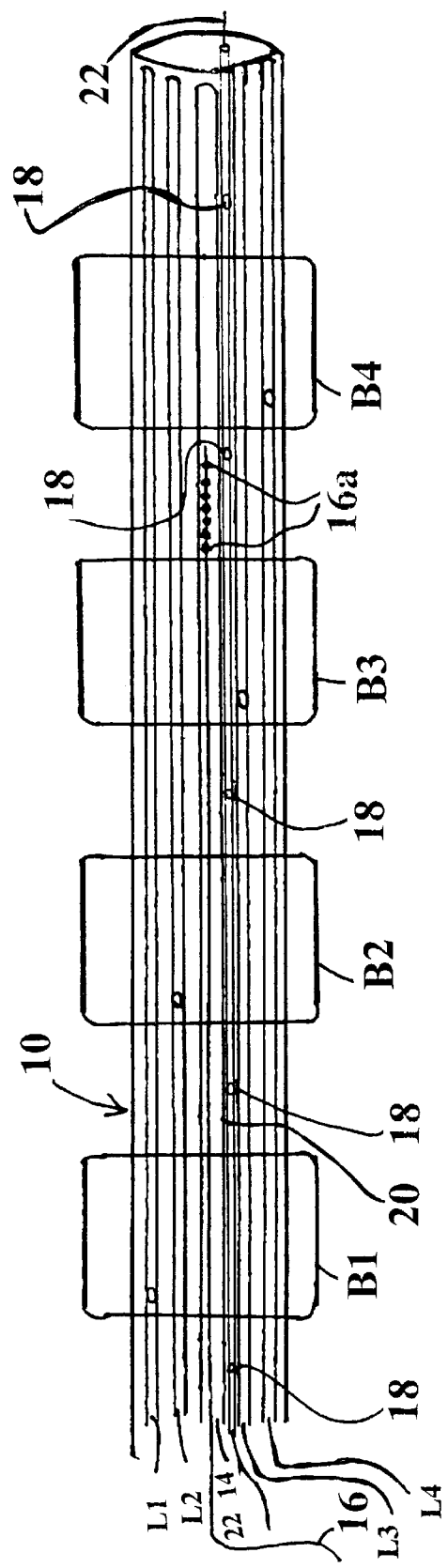
FIG. 1 is a side view, in partial cross-section of a radiation delivery catheter according to the invention, where the balloons are donuts.

Referring to FIG. 1, in one embodiment the present invention comprises a catheter 10 having mounted to its exterior a plurality, i.e. at least two (and in this case four), balloons B1, B2, B3 and B4. Each balloon may be about 2–30 mm long, for example. The balloons may be spaced from each other. Disposed in a central lumen 14 of the catheter is a radiation source, such as a wire 16, which may have pellets 16a mounted thereon. The treatment wire may be controlled from outside the patient to be moved continuously or stepwise within the catheter, with the balloons or balloon segments being selectively sequentially inflated as the radiation source is located within the balloon or balloon-bounded segment. After the radiation source leaves the region interior of a particular balloon or balloon-bounded segment, that balloon or balloon segment is deflated. In this way, only the balloon or balloon segment which encircles or is close to the radioactive source is inflated. Each separately inflatable balloon or balloon-bounded segment is connected to a different lumen for enabling the separate and independent inflation/deflation. This shown in FIG. 1 where lumen L1 connects to balloon B1, and so on. Lumens L1, L2, L3 and L4 are dead end lumens. It is also possible to arrange inflation of a multiplicity of balloons from a common inflation lumen.

Perfusion holes 18 may be provided in communication with a lumen 20 to allow blood to perfuse around any portion of the vein or artery where a balloon or balloon segment is inflated. The lumen 20 may also be used to receive a guidewire 22.

Figure 2:
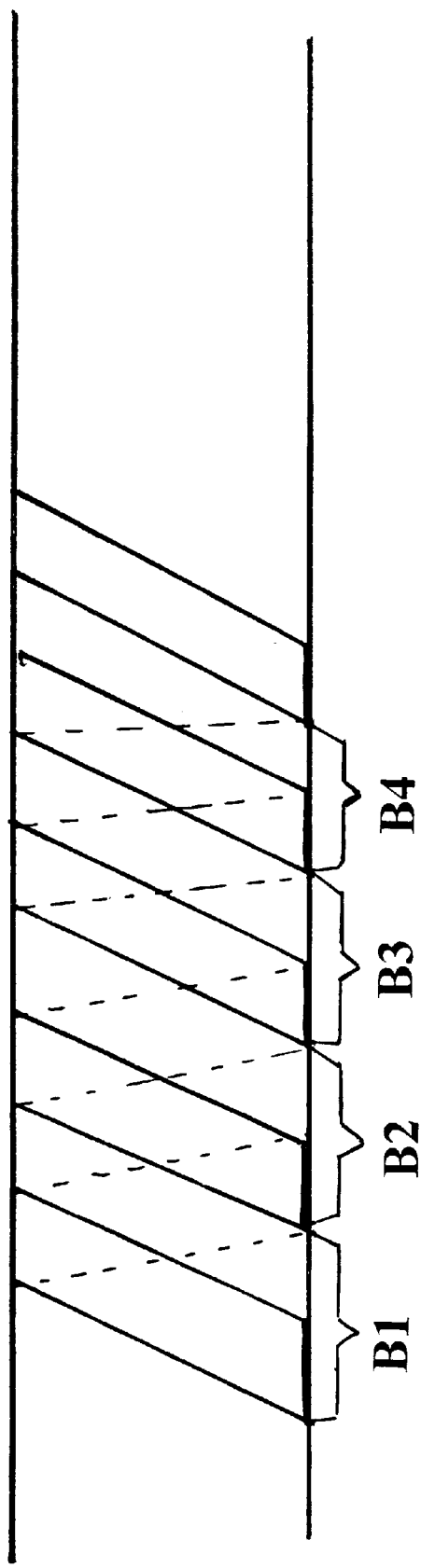
FIG. 2 is a side view in partial cross-section, of another radiation delivery catheter according to the invention, where the balloons are segments of a spiral balloon.

Instead of a plurality of spaced balloons as in FIG. 1, a balloon spirally wound around the catheter may be provided as in FIG. 2, wherein the spiral balloon is segmented with the segments individually inflatable and deflatable. The segments are labeled B1, B2, B3 and B4, defined by the darkened lines. In this configuration, perfusion openings and a dedicated lumen for this purpose are optional.

In a variation, the balloons or balloon segments are inflated two adjacent balloons or segments at a time with the sequence of inflation tracking the movement of the radioactive source whereby a balloon or balloon segment in which the radioactive source is moving away from is deflated, while the balloon or balloon segment which the radioactive source is moving toward is inflated. In the case of four balloons or balloon segments numbered B1, B2, B3, B4, first balloons B1 and B2 are inflated when the radioactive source is disposed therein, then B1 is deflated and B3 is inflated as the source is moved towards B3 and away from B1, followed by B2 being deflated and B4 inflated.

In another embodiment of the invention the plurality of balloons or spiral balloon segments are mounted to an exterior tube into which is slidably received a catheter. The radioactive source is controlled to move within the tube while the tube is held stationary in the patient's vascular structure. The inflation and deflation of the balloons or balloon segments may occur in the same manner as in the first embodiment.

The above arrangements, whereby only selective balloons or balloon segments are inflated, provide for effective centering of the radioactive material in the patient's tubular structure, but does not require all of the balloons or balloon segments along the entire length of the catheter to be inflated at the same time, thereby in the case of artery or vein, allowing blood to perfuse in areas where inflation of balloons or balloon segments is not necessary to achieve centering of the radiation source within the patient's tubular structure.

Although a preferred embodiment, and variations thereof, have been shown and described, numerous variations and modifications will readily occur to those skilled in the art. The invention is not limited to the preferred embodiment and its scope is defined only by the following claims.

I claim:

1. A radiation catheter for treating a luminal structure of a patient, comprising:
    a catheter having at least one centrally disposed lumen adapted to center radioactive material in the luminal structure of the patient said lumen being open throughout its interior to receive a radioactive source;
    a source of radioactive material; and
    at least two balloon segments located at different longitudinal extents of the catheter, said segments being separably inflatable and deflatable.

2. The radiation catheter according to claim 1, further comprising a radiation source movable within the lumen of the catheter, wherein the balloon segment nearest the source is inflatable to center the radiation source radially in the luminal structure, and deflatable when not needed to center the radiation source.

3. The radiation catheter according to claim 1, wherein the balloon segments comprise a plurality of donut shaped or lobulated balloons.

4. The radiation catheter according to claim 1, wherein the balloon segments comprise segments of a balloon spirally wound around the catheter.

5. The radiation catheter according to claim 2, wherein the radiation source is a wire.

6. The radiation catheter according to claim 5, wherein the radiation source comprises radiation pellets mounted on the wire.

7. The radiation catheter according to claim 1, wherein the balloon segments are at least three, and wherein at least two adjacent segments are inflated at the same time.

8. The radiation catheter according to claim 1, wherein the balloon segments are mounted to the catheter.

9. The radiation catheter according to claim 1, further comprising a tube into which the catheter is slidably received, and where the balloon segments are mounted to the tube.

10. The radiation catheter according to claim 1, further including perfusion holes to permit fluid to flow inside the catheter around an inflated balloon segment.

11. A radiation catheter for treating a luminal structure of a patient, comprising:
    a catheter having at least one centrally disposed lumen, said lumen being open throughout its interior to receive a radioactive source; and
    at least two balloon segments located at different longitudinal extents of the catheter, said segments being separably inflatable and deflatable; and
    a radiation source movable within the lumen of the catheter, whereby the balloon segment nearest the source is inflatable to center the radiation source radially in the luminal structure, and deflatable when not needed to center the radiation source.

12. The radiation catheter according to claim 11, wherein the balloon segments comprise a plurality of donut shaped or lobulated balloons.

13. The radiation catheter according to claim 11, wherein the balloon segments comprise segments of a balloon spirally wound around the catheter.

14. The radiation catheter according to claim 11, wherein the radiation source is a wire.

15. The radiation catheter according to claim 14, wherein the radiation source comprises radiation pellets mounted on the wire.

16. The radiation catheter according to claim 11, wherein the balloon segments are at least three, and wherein at least two adjacent segments are inflated at the same time.

17. The radiation catheter according to claim 11, wherein the balloon segments are mounted to the catheter.

18. The radiation catheter according to claim 11, further comprising a tube into which the catheter is slidably received, and where the balloon segments are mounted to the tube.

19. The radiation catheter according to claim 11, further including perfusion holes to permit fluid to flow inside the catheter around an inflated balloon segment.

* * * * *